(12) United States Patent  
Hirai et al.

(10) Patent No.: US 7,201,871 B2  
(45) Date of Patent: Apr. 10, 2007

(54) SPECIMEN HAVING CAPABILITY OF SEPARATING SOLID COMPONENT

(75) Inventors: Kaoru Hirai, Kyoto (JP); Satoshi Yonehara, Kyoto (JP)

(73) Assignee: Arkray Inc., Kyoto (JP)

( * ) Notice: Subject to any disclaimer, the term of this patent is extended or adjusted under 35 U.S.C. 154(b) by 395 days.

(21) Appl. No.: 10/221,644

(22) PCT Filed: Mar. 15, 2001

(86) PCT No.: PCT/JP01/02069

§ 371 (c)(1),  
(2), (4) Date: Sep. 13, 2002

(87) PCT Pub. No.: WO01/69237

PCT Pub. Date: Sep. 20, 2001

(65) Prior Publication Data

US 2003/0044316 A1    Mar. 6, 2003

(30) Foreign Application Priority Data

Mar. 15, 2000  (JP) .............................. 2000-072545

(51) Int. Cl.  
    *G01N 30/00*    (2006.01)
(52) U.S. Cl. .................. 422/56; 422/55; 422/68.1; 422/82.05
(58) Field of Classification Search ................. 422/50, 422/55, 56, 68.1, 82.05, 82.08  
    See application file for complete search history.

(56) References Cited

U.S. PATENT DOCUMENTS

| | | | |
|---|---|---|---|
| 3,046,201 A | * | 7/1962 | White et al. ............. 435/253.6 |
| 4,069,017 A | | 1/1978 | Wu et al. |
| 4,260,392 A | * | 4/1981 | Lee .............................. 435/22 |
| 4,357,363 A | * | 11/1982 | Pierce et al. ............... 435/7.92 |
| 4,421,719 A | * | 12/1983 | Burleigh ...................... 422/57 |
| 4,430,436 A | * | 2/1984 | Koyama et al. ............ 436/531 |

FOREIGN PATENT DOCUMENTS

| | | |
|---|---|---|
| EP | 0 013 156 | 7/1980 |
| GB | 1440464 | 6/1976 |
| JP | 9-054087 | 2/1997 |
| JP | 9-069888 | 4/1997 |
| JP | 2000-65826 | 3/2000 |

* cited by examiner

*Primary Examiner*—Jill Warden  
*Assistant Examiner*—Samuel P. Siefke  
(74) *Attorney, Agent, or Firm*—Wenderoth, Lind & Ponack, L.L.P.

(57) ABSTRACT

A test strip having the capability of separating blood cells from whole blood, wherein it has a porous reagent layer comprising beads, an inorganic gel and a reagent that causes a detectable reaction with a substance to be detected, and a substrate that supports the reagent layer, wherein the beads are adhered to each other with the inorganic gel, and interstices are formed between the beads to trap a solid. The test strip can thus be used for separating blood cells from a whole blood including blood cells and plasma and detecting a substance to be detected, such as glucose, contained in plasma. The use of the test strip allows the measurement of a substance to be detected even by measurement of a transmitted light, the exhibition of good oxygen permeability, and thus can be used for measuring a substance to be detected with improved accuracy.

7 Claims, 2 Drawing Sheets

▨ RED PORTION WHERE WHOLE BLOOD WAS SPOTTED AND BLOOD CELLS REMAINDED

▧ PORTION WHERE PLASMA MIGRATED IN REAGENT LAYER TO COLOR PALE RED

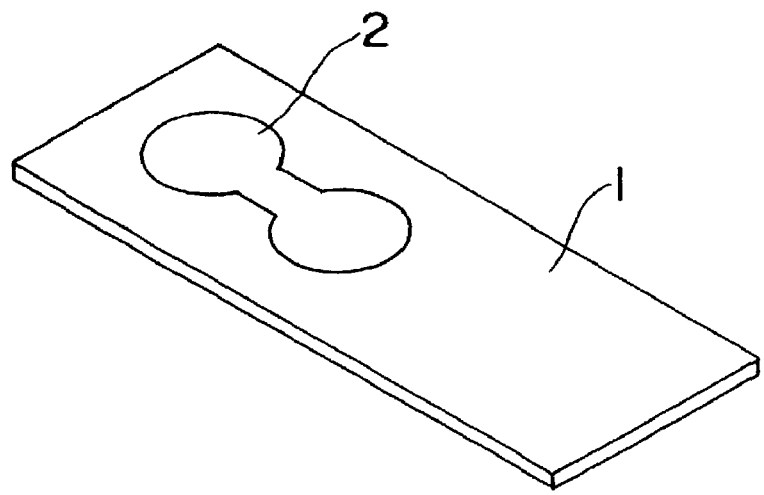
F I G. 1
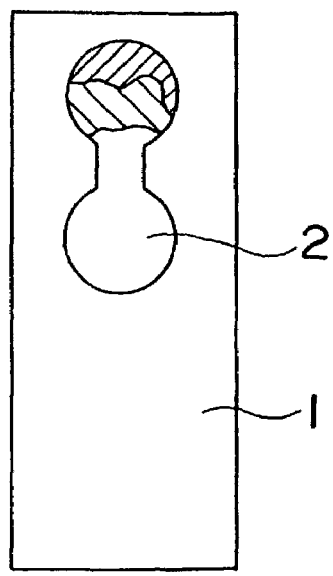
F I G. 2
▨ RED PORTION WHERE WHOLE BLOOD WAS SPOTTED AND BLOOD CELLS REMAINDED
▨ PORTION WHERE PLASMA MIGRATED IN REAGENT LAYER TO COLOR PALE RED

| | RED PORTION WHERE WHOLE BLOOD WAS SPOTTED AND BLOOD CELLS REMAINDED |
|---|---|
| | PORTION WHERE PLASMA MIGRATED IN REAGENT LAYER TO COLOR PALE RED |

| | RED PORTION WHERE WHOLE BLOOD WAS SPOTTED AND BLOOD CELLS REMAINDED |
|---|---|
| | PORTION WHERE PLASMA MIGRATED IN REAGENT LAYER TO COLOR PALE RED |

SPECIMEN HAVING CAPABILITY OF SEPARATING SOLID COMPONENT

This is the U.S. National Phase under 35 U.S.C. § 371 of International Application PCT/JP 01/02069, filed Mar. 15, 2001, which claims priority of JP 2000-72545, filed Mar. 15, 2000. Each of the above applications are incorporated herein by reference in their entirety.

TECHNICAL FIELD

The present invention relates to a test strip suitable for detecting a substance to be detected in blood and belongs mainly to the field of chemical analysis of biological materials.

BACKGROUND ART

In a case where any component included in a biosample such as blood, urine or cerebrospinal fluid is detected, usually a series of analytical processes such as absorption, diffusion, reaction, detection, etc. of a sample fluid are required. In particular, in blood tests using blood including blood cells and plasma (hereinafter, sometimes referred to as "whole blood") where glucose in plasma is to be detected and quantified as a substance to be detected, and so on, it is known that blood cells give various influences on measured results and tend to cause errors. For this reason, in blood tests using whole blood, it has been desired to separate blood cells and plasma. Various proposals have been made on techniques for separating blood cells and plasma from whole blood and detecting a substance to be detected in the separated plasma.

As the above-mentioned techniques, a testing instrument is known which has a mechanism of separating blood cells by centrifugation by utilizing a difference in specific gravity between blood cells and plasma. However, this testing instrument requires a centrifuge so that the device for detecting a substance to be detected becomes complicated and of a large scale and reagents used may become complicated so that there are cases where it is practically undesirable.

On the other hand, as the above-mentioned technique is known a test strip that separates blood cells from whole blood and detects a substance to be detected in plasma by using a coloring reagent that develops a color with the substance to be detected. The test strip is superior to the above-mentioned testing instrument in that it can detect a substance to be detected only by spotting it with whole blood.

As such test strips are known, for example, multi-layered type test strips having overlaid a blood cells separating layer having a porous structure composed of an asymmetric film, a glass filter, or polymer particles fixed with an organic polymer and a reagent layer comprising a coloring reagent that develops a color with a substance to be detected on an optically transparent substrate (for example, JP 49-53888 A, JP 55-90859 A, etc.), and test strips composed of polymer particles fixed with an organic adhesive or the like having suitable interstices between the beads as well as forming a layer comprising the above-mentioned coloring reagent, in which separation of blood cells, development of plasma, and detection of a substance to be detected are performed (for example, JP 57-160063 A, etc.).

However, in the above-mentioned multi-layered type test strip, whole blood tends to spread on the blood cells separating layer and the separation of blood cells and plasma is mainly separation in the vertical direction utilizing their own weights, so that a blood cells layer is formed on the top of the blood cells separating layer. Therefore, for example, when it is intended to quantify a substance to be detected by measurement of transmitted light, if the substance to be detected develops a color by the coloring reagent, there are cases where measuring light is cut off by the above-mentioned blood cells layer to make measurement of transmitted light impossible.

Also, there are cases where a substance to be detected is detected and measured while oxygen is being supplied thereto depending on the substance to be detected. In such cases, the above-mentioned type test strips tend to form a blood cells layer on the blood cells separating layer, resulting in poor permeability to oxygen; for supplying oxygen, it is necessary to provide an oxygen supply means such as an oxygen permeating membrane between a reagent layer and a substrate. To provide the oxygen supply means such as an oxygen permeating membrane to the above mentioned laminate type test strip is difficult and becomes a cause of increasing cost for fabricating the test strip.

Also, in the above-mentioned laminate type test strips, whole blood tends to spread on the blood cells separating layer and the separation occurs mainly in the vertical direction, and hence in order to sufficiently develop the substance to be detected in the reagent layer, it is necessary to spot a sufficient amount of blood to the blood cells separating layer, so that a larger amount of specimen is required for a single measurement.

Also, in the case of, among the above-mentioned multi-layered type test strips, those test strips in which the blood separating layer is formed by fixing polymer particles with an organic polymer, the organic polymer tends to absorb water and swell, the interstices between particles in the blood cells separating layer make too small to develop plasma, so that there may be the case where a sufficient amount of plasma is not developed in the reagent layer.

Also, in the case of the test strips disclosed in JP 57-160063 A, etc., suitable interstices between particles are formed in the layer so that plasma can be developed not only in the vertical direction but also in the horizontal direction due to a capillary action, which is advantageous in performing the above-mentioned measurement of transmitted light. However, because like the above-mentioned multi-layered type test strips, blood cells tend to spread on the reagent layer, there remain problems of the light shielding of the blood cells layer and the deterioration of oxygen permeability associated with formation of the blood cells layer in the measurement of transmitted light. Also, in these test strips, when plasma is developed in the layer, there are cases where dyes and the like generated by the reaction of it with a coloring reagent are further developed so that a deviation may occur in the concentration distribution of the substance to be detected.

Also, since the test strips are produced by fixing polymer particles with an adhesive or the like so that suitable interstices between particles can be formed, their production is complicated and difficult.

DISCLOSURE OF THE INVENTION

The present invention has been made in view of the above-mentioned matters and an object of the present invention is to provide a test strip that can measure a substance to be detected also with the measurement of transmitted light, has better oxygen permeability, and that can measure the substance to be detected at higher precision.

The present invention has the following constructions as means for attaining the object.

That is, the present invention provides a test strip having an ability of separating a solid from a specimen comprising a solid and a liquid to detect a substance to be detected contained in the liquid, which has a reagent layer having a porous structure comprising beads, an inorganic gel, and a reagent that causes a detectable reaction with the substance to be detected, and a substrate that supports the reagent layer, wherein the beads are adhered to each other with the inorganic gel to form interstices between the beads for trapping the solid.

Also, in the present invention, it is preferred that the specimen is blood including blood cells and plasma (whole blood), that the substrate has a hydrophilic area on its surface, and the hydrophilic area supports the reagent layer.

Also, in the present invention, it is preferred that the beads have a particle diameter of 0.5 to 10 µm, and the final concentration of the beads is 1 to 30% by weight, and the final concentration of an inorganic gelling agent that forms the inorganic gel is 0.1 to 3% by weight.

Also, in the present invention, it is preferred that the reagent is a reagent that causes an optical change by reacting with a substance to be detected, and that the substrate is made of a light transmitting substance.

The test strip of the present invention has a reagent layer, and a substrate that supports the reagent layer.

The reagent layer has porous structure comprising beads, an inorganic gel, and a reagent that causes a detectable reaction with a substance to be detected. In the reagent layer, the beads are adhered to each other with the inorganic gel to form interstices between the beads for trapping the solid.

While the beads may be any one as far as they can trap the solid in the interstices between the beads, those having a narrow particle size distribution within the above-mentioned particle diameter range are preferred in separating the solid. Also, in the case where beads having a wide particle size distribution are used or where beads having a relatively large particle diameter are used, it is preferred that beads having small particles having a relatively small particle diameter as small as 10 µm or less are used in forming suitable interstices between the beads.

A suitable particle diameter of the beads may vary depending on the size of the solid (for example, the above-mentioned blood cells, etc.) to be caught in the interstices between the beads. While it is possible to use beads having a particle diameter of about 30 µm, the particle diameter is preferably 0.5 to 10 µm, more preferably 3 to 8 µm. If the particle diameter of the beads is too small as compared with the above-mentioned range, there are cases where developing of the liquid may not be performed smoothly while if the particle diameter of the beads is too large as compared with the above-mentioned range, there are cases where the trapping of the solid may not be performed sufficiently.

Although suitable content of the beads in the reagent layer may vary depending on the desired distance of developing the liquid or on the suitable thickness of the reagent layer, it is preferably 1 to 30% by weight as a final concentration. If the content of the beads is too small as compared with the above-mentioned range, there are cases where the thickness of the reagent layer may become insufficient while if the content of the beads is too large as compared with the above-mentioned range, there are cases where the thickness of the reagent layer may become larger than is required.

Also, it is preferred that the above-mentioned beads have a shape as close to a sphere as possible in order to form good interstices between the beads. In the present invention, any beads regardless of the kind may be used suitably as far as they satisfy the above-mentioned conditions. As such beads, for example, inorganic beads such as glass beads, polymerized beads such as latex beads, etc. may be exemplified. Among these, it is more preferable that polymerized beads, which are easy to control particle diameter, shape of particle, and particle size distribution upon production, are used. It is possible to get such polymerized beads by purchasing commercial products. It is also possible to produce them by a conventional method such as a suspension polymerization method or an emulsion polymerization method.

The above-mentioned inorganic gel is to bond the above-mentioned beads to each other to make the reagent layer has a porous structure. Since generally the inorganic gels hardly swell when they absorb water as compared with organic gels, they have advantages, for example, in that the cell length (thickness of the reagent layer) is more likely to be retained constant when a substance to be detected is measured by measurement of transmitted light and that the interstices between the beads in the reagent layer during the developing of the liquid are more likely to be retained constant.

Also, since the inorganic gelling agent for forming inorganic gels generally tends to adsorb compounds having polar substituents, dyes, etc., they tend to adsorb the above-mentioned reagent and reaction products (dye, etc.) between the reagent and a substance to be detected, so that it is advantageous in that deviation of concentration distribution of the detected substance to be detected hardly occurs.

Furthermore, if the inorganic gel is a gel that has thixotropic property, the fluidity at the time of forming an inorganic sol is excellent and hardens by keeping still (gelling). Therefore these are suitable in forming a reagent layer on the above-mentioned substrate. Also, the inorganic gel becoming transparent by addition of water is suitable in detecting a substance to be detected by an optical change.

While a suitable content of the inorganic gelling agent in the above-mentioned reagent layer may vary depending on the amount of beads to be used and the properties (gelling capability, etc.) of the inorganic gelling agent to be used, it is preferably 0.1 to 3% by weight as a final concentration. If the content of the inorganic gelling agent is too small as compared with the above-mentioned range, the bonding between the beads becomes insufficient, so that there are cases where no reagent layer can be formed. If the content of the inorganic gelling agent is too large as compared with the above-mentioned range, there are cases where an excessive inorganic gelling agent fills in the interstices between the beads, giving bad influences on the developing of the liquid.

As the above-mentioned inorganic gelling agent may be used generally used inorganic gelling agents and for example, Laponite series (produced by Nippon Silica Industrial Co., Ltd.), Lucentite SWN, and SWF (produced by Co-op Chemical Co., Ltd.), Thixopy W (produced by Kyowa Chemical Co., Ltd.), Smecton SA, and Kunipia (produced by Kunimine Industries Co., Ltd.), Multigen (produced by Hojun Kogyo Co., Ltd.) and so on can be exemplified.

The above-mentioned reagents can be found widely in compounds, such as dye precursors, that form optically detectable substances such as dyes and fluorescent dyes, oxidized forms or reduced forms of electron transfer substances electrochemically detectable, or compounds that form complex compounds, by oxidation-reduction reaction, acid-base reaction, condensation reaction, complex formation reaction, etc.

First, specific explanation will be made on reagents that form optically detectable substances.

As the above-mentioned dye precursors, preferably compounds having a conjugated system such as an aromatic ring are used. For example, reagents that form a quinone dye by oxidative condensation between a coupler, represented by 4-amino-1,2-dihydro-1,5-dimethyl-2-phenyl-3H-pyrazol-3-one (hereinafter, abbreviated as "4-AA"), and a hydrogen donor; dye precursors that form oxidized coloring dye, such as o-tolidine and benzidine; dye precursors that form colors by being oxidized, such as leuco forms of dyes; reagents that form fluorescent substances by being oxidized; luminescent materials, such as chemiluminescent materials; reagents that form dyes by being reduced, such as tetrazolium salts; diazonium salts that forms azo dyes as a result of a change in pH; reagents for color reaction; reagents for generation reaction of fluorescent substances; enzyme substrates that form dyes or fluorescent substances with enzymes; compounds that form complexes and develop colors or change colors; and so on can be exemplified.

The above-mentioned hydrogen donor is a compound such as a phenol that generates a quinone dye by condensing with 4-AA or 3-methyl-2-benzothiazolinone hydrazone under the coexistence of oxidizing agents. Specific examples of the hydrogen donors include dichlorophenol; o-methoxyphenol; 1,2,3-trihydroxybenzene; dimethylaniline; N-ethyl-N-sulfopropyl-m-anisidine; N-ethyl-N-sulfopropylaniline; N-ethyl-N-(3-sulfopropyl)-3,5-dimethoxyaniline; N-ethyl-N-(3-sulfopropyl)-3,5-dimethylaniline; N-ethyl-N-sulfopropyl-m-toluidine; N-ethyl-N-(2-hydroxy-3-sulfopropyl)-m-anisidine; N-ethyl-N-(2-hydroxy-3-sulfopropyl) aniline; N-ethyl-N-(2-hydroxy-3-sulfopropyl)-3,5-dimethoxyaniline; N-(2-hydroxy-3-sulfopropyl)-3,5-dimethoxyaniline; N-ethyl-N-(2-hydroxy-3-sulfopropyl)-3,5-dimethylaniline; N-ethyl-N-(2-hydroxy-3-sulfopropyl)-m-toluidine; N-(3-sulfopropyl)aniline; and the like.

Examples of the above-mentioned o-tolidines and benzidines include: o-tolidine; dianisidine; 3,3'-diaminobenzidine; 3,3',5,5'-tetramethylbenzidine; N-(3-sulfopropyl)-3,3', 5,5'-tetramethylbenzidine; and the like.

The above-mentioned leuco form is a colorless dye precursor that becomes a dye by being oxidized and develops color. Examples of the dye generated by oxidizing the leuco form include: 2,6-dichloro-4-[(4-hydroxyphenyl)imino]-2, 5-cyclohexadiene-1-one; 2,6-dichloro-4-[(3-chloro-4-hydroxyphenyl)imino]-2,5-cyclohexadiene-1-one; 7-(diethylamino)-3-imino-8-methyl-3H-phenoxazine salts; 3-(diethylamino)-7-amino-5-phenylphenazinium salts; 3,7-bis(dimethylamino)phenothiazin-5-ium salts; 1-hydroxy-5-methylphenazinium salts; 7-hydroxy-3H-phenoxazin-3-one-10-oxide, and the like.

Examples of the leuco form include: 4,4'-benzylidenebis(N, N-dimethylaniline); 4,4'-bis[N-ethyl-N-(3-sulfopropylamino)-2,6-dimethylphenyl]methane; 1-(ethylaminothiocarbonyl)-2-(3,5-dimethoxy-4-hydroxyphenyl)-4,5-bis(4-diethylaminophenyl)imidazole; 4,4'-bis(dimethylamino) diphenylamine; N-(carboxymethylaminocarbonyl)-4,4'-bis (dimethylamino)diphenylamine salts; 10-(carboxymethylaminocarbonyl)-3,7-bis(dimethylamino) phenothiazine salts, and the like.

Other examples of the dye precursor that develops color by being oxidized include: 4-methoxyphenol; 4-ethoxyphenol; 2-ethoxyphenol; 1-(2-hydroxy-5-methoxyphenyl)ethanone; 2-hydroxy-5-methoxybenzoic acid; 2-hydroxy-5-methoxybenzaldehyde; methyl 2-hydroxy-5-methoxybenzoate; 4-methoxy-2-nitrophenol; 2-chloro-4-methoxyphenol; 4-hydroxy-3-methoxybenzaldehyde; 4-hydroxy-3-methoxybenzoic acid, and the like.

Also, another example of the dye precursor include: 3-(4-hydroxyphenyl)-2-propenoic acid; 2-hydroxyphenylacetic acid; 3-hydroxyphenylacetic acid; 4-hydroxyphenylacetic acid; 3-hydroxybenzoic acid; 4-hydroxybenzoic acid; 2-aminobenzoic acid; 3-aminobenzoic acid; 4-aminobenzoic acid; 3,4-diaminobenzoic acid; 3,5-diaminobenzoic acid; 4-amino-2-chlorobenzoic acid; 4-amino-3-methylbenzoic acid; 4-amino-3-methoxybenzoic acid; 4-aminophthalic acid, and the like.

Moreover, examples of the dye precursor include: 2,4-diamino-6-hydroxypyrimidine; 4,5-diamino-6-hydroxypyrimidine; 4-amino-2,6-dihydroxypyrimidine; 6-hydroxy-2,4, 5-triaminopyrimidine; 4,5-diamino-2,6-dihydroxypyrimidine; 4-amino-6-hydroxy-2-methylpyrimidine; 4-amino-6-hydroxy-2-methoxypyrimidine, and the like.

Examples of the above-mentioned reagents that form fluorescent substance by being oxidized include: 4-hydroxyphenylacetic acid; (4-hydroxy-3-methoxyphenyl)acetic acid; 3-(4-hydroxyphenyl)propionic acid; 4-hydroxy-(2-aminoethyl)phenol; 4-hydroxy-N,N,N-trimethylbenzenemethaminium; .-amino-p-hydroxyhydrocinnamic acid; 4-hydroxyphenethylamine; N-(4-hydroxyphenyl)acetanilide; 2,7-dichlorofluorescein diacetate, and the like.

In oxidation reactions where dyes as mentioned above are generated, oxidizing agents such as hydrogen peroxide and oxidizing enzymes such as peroxidase are preferably used as oxidizing agents that participate in the oxidation reactions. However, of course, the oxidizing agents that participate in the above-mentioned oxidation reactions are not limited thereto but may be various known oxidizing agents and oxidizing enzymes.

Examples of the above-mentioned luminescent materials such as the chemiluminescent materials include: Firefly luciferin; Cypridina luciferin; aequorin; lucigenin derivatives; luminol derivatives; acridinium esters; peroxalate, and the like.

Examples of the tetrazolium salts include: 2,3,5-triphenyltetrazolium salts; 2,5-diphenyl-3-(1-naphthyl)-2H-tetrazolium salts; 3,3-[3,3'-dimethoxy-(1,1'-biphenyl)-4,4'-diyl]-bis[2-(4-nitrophenyl)-5-phenyl-2H-tetrazolium] salts; 3,3-[3,3'-dimethoxy-(1,1'-biphenyl)-4,4'-diyl]-bis[2,5-diphenyl-2H-tetrazolium] salts; 2-(4-iodophenyl)-3-(4-nitrophenyl)-5-phenyl-2H-tetrazolium salts; 2-(4-iodophenyl)-3-(4-nitrophenyl)-5-(2,4-disulfophenyl)-2H-tetrazolium salts; 2-(4-iodophenyl)-3-(2,4-dinitrophenyl)-5-(2,4-disulfophenyl)-2H-tetrazolium salts; 3,3'-(1,1'-biphenyl-4,4'-diyl)-bis (2,5-diphenyl-2H-tetrazolium) salts; 3-(4,5-dimethyl-2-thiazolyl)-2,5-diphenyl-2H-tetrazolium salts, and the like.

Examples of the compounds that generates a dye by being reduced include reduced forms such as 1,1'-dimethyl-4,4'-bipyridilium salts, and 1,1'-dibenzyl-4,4'-bipyridilium salts. Also, 7-hydroxy-3H-phenoxazin-3-one-10-oxide, or the like, generates a fluorescent dye by being reduced. Examples of such reagents that generate a fluorescent dye include fluorescent substances which are generated by reducing 7-hydroxy-3H-phenoxazin-3-one-10-oxide, 5-cyano-2,3-bis (4-methylphenyl)-2H-tetrazolium salts, 2,3-bis(4-cyanophenyl)-5-cyano-2H-tetrazolium salts, etc.

In the reduction reactions where such dyes are generated, nicotinamide adenine dinucleotide (NAD), nicotinamide adenine dinucleotide phosphate, etc. are preferably used as reducing agents that participate in the reduction reactions. However, the reducing agents that participate in the above-mentioned reduction reactions are not limited thereto but may be various known reducing agents and reducing enzymes.

Examples of the above-mentioned compounds that can develop color or change color by pH change include: sulfonephthalein dyes such as bromocresol green, bromophenol blue, phenol red, bromopyrogallol red, and pyrogallol red; triphenylmethane dyes such as malachite green, and rosolic acid; quinoline dyes such as quinaldine red, and N-(p-hydroxyphenyl)-2,6-dichloro-p-benzoquinoneimine; oxazone dyes such as 7-hydroxy-3H-phenoxazin-3-one-10-oxide; coumarin dyes such as 6,7-dihydroxy-4-methylcoumarin; electrically-conductive polymeric compounds such as aniline oligomers.

Examples of the above-mentioned diazonium salts include: 2-methoxy-4-morpholinobenzenediazonium salts that generate azo dyes by coupling with indoxyl; 3,3'-dimethoxybiphenyl-4,4'-diazonium salts that generate azo dyes by coupling with urobilinogen, etc. In this category, there are also reagents involved in the reactions for generating diazonium salts. Examples of such reagents include: 4-aminobenzenearsonic acid that generates a diazonium salt in the presence of a nitrite; N-1-naphthylethylenediamine that generates an azo dye by coupling with the above-mentioned diazonium salt, etc. Further, other examples of such reagents include: 2,4-dichloroaniline that generates an azo dye by coupling in the presence of a nitrite; and N,N-diethyl-N'-1-naphthylnaphthylethylenediamineoxalate salts (Tsuda reagent). Nitrites are also included.

Examples of the above-mentioned reagents for color reaction include, but not limited to hydrogen peroxide and 1,4-diaminobenzene for detecting an aldehyde; 2,3-dimethyl-2,3-bis(hydroxyamino)butane for detecting an aldehyde; 3-methyl-2-benzothiazolinone hydrazone and an oxidizing agent for detecting an aldehyde; 1OH-phenothiazine and bromine for detecting a secondary amine; 2,2'-dithiopyridine for detecting a thiol, and the like.

Examples of the above-mentioned reagents for reactions of generating the fluorescent substances include, but are not limited to 2-hydroxy-1,2-diphenylethanone for detecting a guanidino compound; o-phthalaldehyde for detecting histamine; o-phthalaldehyde for detecting spermidine; 1,2-diamino-4,5-dimethoxybenzene for detecting an .-keto acid, and the like.

Examples of the above-mentioned enzyme substrates that react by enzymes form dyes or fluorescent substances include, but are not limited to: N-tosyl-L-phenylalanine-2-methylacridone as a substrate of chymotrypsin; L-alanine-2-methylacridone as a substrate of aminopeptidases; 7-acetoxy-N-methylquinolinium salts for measuring esterases; 7-acetoxy-3H-phenoxazin-3-one as a substrate of esterases; 4-methylumbeliferil phosphate as a substrate of phosphatases; 5,10,15,20-tetrakis(4-phosphonooxyphenyl)porphin as a substrate of phosphatases, and the like. Additionally, the enzyme and the enzyme substrate may chemically bond to, for example, an antibody or fragment thereof.

The above-mentioned compounds that form complexes and develop color or change color include compounds such as a ligand, that may form a complex with a metal ion or an anion by a coordinate bond or an ionic bond, and that may generate dyes or fluorescent substances, and the like. Examples of the compounds that can develop color or change color by forming complexes with metal ions include compounds known as metal indicators or chromoionophores, as well as compounds that may color by forming complexes with colored transition metal ions. Specific examples of such compounds include: ethylenediaminetetraacetic acid; 2,2-bipyridine; 1-hydroxy-2-(2-hydroxyphenylazo)benzene; dibenzo-18-crown-6; dicyclohexyl-18-crown-6; cyclic polyamines; calix[4]arene; 3-[N,N-bis(carboxymethyl)aminomethyl]-1,2-diydroxyanthraquinone; 5',5"-dibromopyrogallol sulfonephthalein; 2-hydroxy-1-(1-hydroxy-2-naphthylazo)-6-nitro-4-naphthalene sulfonate; 2,6-dichloro-4'-hydroxy-3',3"-dimethylfuchson-5',5"-dicarboxylate; 3,3'-bis[N,N-bis(carboxylmethyl)aminomethyl]fluorescein; 8-[N,N-bis(carboxylmethyl)aminomethyl]-4-methylumbelliferone; 2,7-bis(2-arsonophenylazo)-1,8-dihydroxy-3,6-naphthalenedisulfonic acid; 5-chloro-2-hydroxy-3-(2,4-dihydroxyphenylazo)benzenesulfonic acid; 5-[(hexahydro-2,4,6-trioxo-5-pyrimidinyl)imino]-2,4,6(1H,3H,5H)-pyrimidinetrione salts; 2-(5-bromo-2-pyridylazo)-5-[N-propyl-N-(3-sulfopropyl)amino]aniline salts; 1,8-dihydroxy-2-(2-pyridylazo)-3,6-naphthalenedisulfonate; 2-nitroso-5-[N-propyl-N-(3-sulfopropyl)amino]phenol, and the like.

Also particularly, examples of the compounds that may form colored complexes with monovalent cations include: tetrakis[3,5-bis(trifluoromethyl)phenyl]borate salts; tetraphenyl phosphonium salts; and the like.

Also particularly, examples of the compounds that may form fluorescent complexes with calcium ions, etc. include: 1-[2-amino-5-(2,7-dichloro-6-hydroxy-3-oxy-9-xanthenyl)phenoxy]-2-(2-amino-5-methylphenoxy)ethane-N,N,N',N'-tetraacetate; pentaacetoxymethyl 1-[2-amino-5-(2,7-dichloro-6-hydroxy-3-oxy-9-xanthenyl)phenoxy]-2-(2-amino-5-methylphenoxy)ethane-N,N,N',N'-tetraacetate; 1-[6-amino-2-(5-carboxy-2-oxazoyl)-5-benzofuranyloxy]-2-(2-amino-5-methylphenoxy)ethane-N,N,N',N'-tetraacetate; pentaacetoxymethyl 1-[6-amino-2-(5-carboxy-2-oxazoyl)-5-benzofuranyloxy]-2-(2-amino-5-methylphenoxy)ethane-N,N,N',N'-tetraacetate; 1-[2-amino-5-(6-carboxy-2-indolyl)phenoxy]-2-(2-amino-5-methylphenoxy)ethane-N,N,N',N'-tetraacetate; pentaacetoxymethyl 1-[2-amino-5-(6-carboxy-2-indolyl)phenoxy]-2-(2-amino-5-methylphenoxy)ethane-N,N,N',N'-tetraacetate; 8-amino-2-[(2-amino-5-methylphenoxy)methyl]-6-methoxyquinoline-N,N,N',N'-tetraacetate; pentaacetoxymethyl 8-amino-2-[(2-amino-5-methylphenoxy)methyl]-6-methoxyquinoline-N,N,N',N'-tetraacetate; 3,3'-bis[N,N-bis(carboxymethyl)aminomethyl]fluorescein; 8-[N,N-bis(carboxymethyl)aminomethyl]-4-methylumbelliferone, and the like.

Furthermore, tetraphenylarsonium salts that form colored complexes with anions, N-ethoxycarbonylmethyl-6-methoxyquinolinium bromide that form complexes with chloride ions to decrease the fluorescence intensity, 8-hydroxy-1-(salicylidenamino)-3,6-naphthalenedisulfonates that form complexes with boron, etc. may also be included.

Specifically the above-mentioned reagents to substances to be detected are exemplified as follows: in case where the substance to be detected is glucose, glucose oxidase, peroxidase, 4-AA, and N-methyl-N-(2-hydroxy-3-sulfopropyl)-3,5-dimethylaniline; in case where the substance to be detected is cholesterol, cholesterol oxidase, peroxidase, 4-AA, and N-methyl-N-(2-hydroxy-3-sulfopropyl)-3,5-dimethylaniline; in case where the substance to be detected is lactic acid, lactate dehydrogenase, $NAD^+$, diaphorase, and tetrazolium violet; and in case where the substance to be detected is alkaline phosphatase, p-nitrophenyl phosphate, respectively.

Then, specific explanation will be made on reagents that form electrochemically detectable substances.

The electrochemically detectable reagents include, for example, oxidized form or reduced forms of electron transfer substances, ligands that form complex compounds by forming ionic bonds or coordinate bonds to specific ions, and so on.

The electron transfer substances are chemical substances that oxidize or reduce a substance to be detected with an enzyme or the like, where they receive or donate electrons directly or indirectly from or to the substance to be detected. A substance to be detected can be quantified from an electrochemical response when a reduced form or oxidized form of such an electron transfer substance is oxidized or reduced on an electrode.

Specifically, electron transfer substances include: 1,1-dimethyl-4,4'-bipyridilium salts; 1,1'-dibenzyl-4,4'-bipyridilium salts; 1,4-diaminobenzene; 2-methyl-1,4-naphtoquinone; N-methylphenadinium salts; 1-hydroxy-5-methylphenadinium salts; 1-methoxy-5-methylphenadinium salts; 9-dimethylaminobenzo-.-phenoxazin-7-ium salts; ferrocene derivatives; hexacyano iron(II) salts; 7-hydroxy-3H-phenoxazin-3-one-10-oxide; 3,7-diamino-5-phenylphenadinium salts; 3-(diethylamino)-7-amino-5-phenylphenadium salts; 1,4-benzenediol; 1,4-dihydroxy-2,3,5-trimethylbenzene; N,N,N',N'-tetramethyl-1,4-benzenediamine; .2,2'-bi-1,3-dithiol; 2,6-dimethylbenzoquinone; 2,5-dimethylbenzoquinone; 2,3,5,6-tetramethyl-2,5-cyclohexadiene-1,4-dione; 2,6-dichloro-4-[(4-hydroxyphenyl)imino]-2,5-cyclohexadiene-1-one; 2,6-dichloro-4-[(3-chloro-4-hydroxyphenyl)imino]-2,5-cyclohexadiene-1-one; 7-(diethylamino)-3-imino-8-methyl-3H-phenoxazine salts; 3,7-bis(dimethylamino) phenothiazine-5-ium salts, and the like.

Examples of the ligand, specifically the ligand which forms complexes with a cation, include: tetrakis[3,5-bis(trifluoromethyl)phenyl]borate salts; tetraphenylphosphonium salts; valinomycin; cyclo(N',N'-dioctyl-D-asparaginyl-L-prolyl-L-alanyl)$_2$; bis(benzo-15-crown-5); bis[(benzo-15-crown-5)-4-methyl]pimelate; bis(12-crown-4); bis[(12-crown-4)methyl]-2-dodecyl-2-methylmalonate; 14-crown-4; dodecyl-methyl-14-crown-4; 6,6-dibenzyl-1,4,8,11-tetraoxacyclotetradecane; dibenzo-18-crown-6; dicyclohexyl-18-crown-6; 4,16-di-N-octadecylcarbamoyl-3-oxabutyryl-1,7,10,13,19-pentaoxa-4,16-diazacyclohenicosane, and the like.

The ligand that forms complexes with anions include tetraphenylarsonium salts, 6-methoxy-N-(3-sulfopropyl) quinolinium salts, etc.

While in the foregoing, the reagents comprised in the reagent layer have been specifically explained, in addition to the above-mentioned beads, the inorganic gel and the reagent, the reagent layer may comprise usually used additives, etc. as far as they do not inhibit the capability of separating the solid of the reagent layer and reaction between the substance to be detected and the reagent.

For example, in the case where the above-mentioned specimen is human blood, the solid is blood cells and the liquid is plasma. In this case, while the longer diameter of erythrocytes in blood cells is 6 to 9 μm at isotonicity, there are cases where the size and condition of erythrocytes change as a result of a change in salt concentration or pH of the reagent and the erythrocytes cannot be caught in the interstices between the beads in the reagent layer if the pH and salt concentration of the reagent layer is inappropriate. As additives that are suitably used in such occasions, for example, buffers such as bis-tris buffers (buffers prepared from bis(2-hydroxyethyl)imino-Tris(hydoxymethyl)methane and hydrochloric acid), phosphate buffers, citrate buffers, and N-(2-acetamide)imino diacetate buffers; and neutral salts such as sodium chloride, etc. can be exemplified.

Also, in the case where a substance to be detected is detected by measurement of reflected light by utilizing an optical change, a substrate made of a light transmitting substance is used as the substrate and as the additive, powder of titanium oxide or the like that increases the reflectivity of measuring light by reflecting or scattering the measuring light can be exemplified.

Also, a surfactant may be used as an additive to improve the developing of the liquid. Examples of such surfactants include: sugar-alkyl ethers such as n-octyl-.-D-glucopyranoside; sugar-alkyl thioethers such as n-octyl-.-D-thioglucopyranoside and n-heptyl-.-D-thioglucopyranoside; sugar amides such as n-octanoyl-N-methylglucamide and n-nonanoyl-N-methylglucamide; sugar esters such as .-D-fructopyranosyl-.-D-glucopyranoside monodecanoate; N,N-bis(3-D-gluconamidopropyl)deoxycholamide.

The thickness of the reagent layer influences the developing distance of the liquid, with a tendency that a greater thickness gives a greater developing distance of the liquid while a smaller thickness gives a smaller developing distance of the liquid. Therefore, while a suitable thickness of the reagent layer may vary depending on a desired developing distance of the liquid, it is preferably 5 to 130 μm, more preferably 30 to 100 μm, still more preferably 50 to 90 μm. If the thickness of the reagent layer is too small as compared with the above-mentioned range, there are cases where the developing of the liquid is not performed sufficiently so that precise detection or measurement of a substance to be detected is hindered while if the thickness of the reagent layer is too large as compared with the above-mentioned range, there are cases where a large amount of specimen is required for detecting a substance to be detected.

The above-mentioned substrate is not particularly limited with respect to the shape or material thereof as far as it can support the above-mentioned reagent layer. However, it is preferred that the substrate has a hydrophilic area on its surface and supports the reagent layer on this hydrophilic area. As the reason for this, it is believed that the above-mentioned hydrophilic area gives a great influence on the developing of the liquid after a specimen is spotted to the reagent layer.

The liquid is developed in the reagent layer by developing in the vertical direction due to its own weight and by developing in the vertical direction and in the horizontal direction due to a capillary action. On the other hand, the above-mentioned hydrophilic area has good affinity for water and weakens the surface tension of the liquid, which is water-soluble. Therefore, the hydrophilic area acts on the liquid in the reagent layer to cause it to flow in the horizontal direction and it is believed that this action of the hydrophilic area develops the liquid in a downwardly slanting direction. Also, the action of the hydrophilic area toward the horizontal direction has a large area of application and operates only in the horizontal direction, so that it is believed that it makes a contribution to the developing of the liquid in the horizontal direction greater than that made by the capillary action. As a result, in the case where a substance to be detected in whole blood is measured by measurement of transmitted light or some other cases, the substance to be detected can be detected at a position remoter in the horizontal direction of the reagent layer from the site where blood cells, which interferes the detection of the substance to be detected, is attached; this is preferable for performing measurement of transmitted light.

It is preferred that the substrate has a hydrophilic area and a hydrophobic area. The hydrophilic area, when it is formed in a suitable size and shape (for example, a polygon, a quadrate, a circle, an ellipse, a shape resulting from combinations thereof, or the like), can make the size of the reagent layer a suitable one, and hence it is preferred. Also, the substrate having a hydrophilic area and a hydrophobic area may be fabricated by subjecting a hydrophilic material to hydrophobicizing treatment, such as coating the hydrophilic material with a hydrophobic substance such as a silicone or oil or by subjecting a hydrophobic material to a hydrophilicizing treatment.

The substrate, when it is made of a light transmitting substance, is preferable since it enables measurement by measurement of transmitted light in the case where a substance to be detected is detected by an optical change. As the above-mentioned light transmitting substance, for example, inorganic compounds such as glass, organic polymer compounds such as transparent plastics, etc. can be exemplified.

Of these, the organic polymer compounds such as transparent plastics, even if they are hydrophobic polymers, may be subjected to a hydrophilicizing treatment of their surface by irradiation of ultraviolet rays, treatment with silanol, etc. By performing such a hydrophilicizing treatment, transparent plastics can be suitably used as substrates. As such organic polymer compounds can be exemplified readily available organic polymer compounds, for example: polyolefin resins such as polyethylene, polypropylene, and polyfluoroethylene; polystyrene; polyethylene terephthalate, etc.

The test strip of the present invention can be fabricated by coating on the above-mentioned substrate an inorganic sol (a colloidal solution in which an inorganic gelling agent is dispersed) having the above-mentioned reagent uniformly dispersed or dissolved therein and having the above-mentioned beads uniformly dispersed therein in the form of a layer. The above-mentioned beads may be dispersed in the inorganic sol or may be dispersed in the inorganic sol by preliminarily mixing powder of an inorganic gelling agent with beads, and adding in this mixed powder water or a water-based dispersing medium in which the above-mentioned reagent is uniformly dispersed or dissolved. Also, the above-mentioned reagent may be uniformly dispersed or dissolved in the above-mentioned inorganic sol or preliminarily uniformly dispersed or dissolved in a water-based dispersing medium before the addition of the inorganic gelling agent.

Also, the layer formation of the above-mentioned inorganic sol on the substrate may be performed by usually used methods. For example, the layer may be formed by coating uniformly and to a predetermined thickness by using a doctor knife or the like. However, it is preferred to provide a hydrophilic area patterned into a predetermined shape on a substrate and supply to the hydrophilic area an inorganic sol in a suitable amount depending on the area of the hydrophilic area since the inorganic sol can spread on the hydrophilic area to form a reagent layer having a uniform thickness on the substrate.

The reagent layer can be formed by removing water from the inorganic sol provided on the above-mentioned substrate to an extent that the properties of the inorganic gel that adhere the beads cannot be deteriorated. The removal of water from the inorganic sol may be performed by drying under conditions which denaturation, etc. of the reagent can be prevented and the detection results of the substance to be detected cannot be hindered; the drying conditions may vary depending on the kind of reagent, and, for example, drying at 25° C., drying at 40 to 50° C., drying under a reduced pressure condition, drying under a low temperature condition (for example, around 5° C.), or drying under a condition of a combination of these, etc. may be exemplified. In the case where the reagent to be used is susceptible to denaturation, it is generally preferred in inhibiting denaturation of the reagent that the inorganic sol is dried under a low temperature condition.

The test strip of the present invention can detect a substance to be detected by spotting a specimen containing the substance to be detected in at least the liquid to a suitable location on the reagent layer and detecting a reaction between the substance to be detected that is developed in the reagent layer and the reagent.

The specimen that is a target of the test strip of the present invention may be a specimen composed of a liquid alone that includes no solid but it is more preferred that the test strip of the present invention is utilized in the analysis of a specimen that includes the solid and the liquid since it has a capability of separating the solid, which separates the solid in the specimen and detects the substance to be detected in the liquid. As such the specimen, for example, as described above, blood including blood cells as the solid and plasma as the liquid (whole blood) can be exemplified. Also, the test strip of the present invention may be utilized in the analysis of, in addition to whole blood, biological materials (biosamples) such as urine, foods, drugs, trace substances occurring in nature, industrial chemical substances, trace substances in wastes, and the like.

Here, one example in which the specimen is whole blood is shown and the state of the test strip of the present invention at the time of analysis of the specimen will be explained.

Since the reagent layer in the test strip of the present invention is a porous structure formed by the above-mentioned beads, the above-mentioned inorganic gel, and the above-mentioned reagent, spotting whole blood on the reagent layer allows blood cells to remain on the reagent layer and plasma to develop in the horizontal direction in the reagent layer from the spotted site. On this occasion, since the reagent layer comprises the inorganic gel, the whole blood spotted on the reagent layer hardly develops on the reagent layer and blood cells hardly spread on the reagent layer. As a result, the substance to be detected in plasma can be detected at a location developed to some extent in the horizontal direction from the site on the reagent layer where blood cells are attached and hence the measuring light is not shielded by blood cells, so that the substance to be detected can be measured by measurement of transmitted light. Also, since blood cells hardly spread on the reagent layer, a blood cells layer is hardly formed on the reagent layer and since it is of a porous structure, the reagent layer is excellent in oxygen permeability. Also, since blood cells hardly spread on the reagent layer, and since plasma develops in the horizontal direction in the reagent layer, the reagent layer can detect the substance to be detected with a specimen in a smaller amount than is required in the above-mentioned multi-layered type test strips.

Also, since in the reagent layer, the beads are adhered with the inorganic gel to form a porous structure, the reagent in the reagent layer, a reaction product between the reagent and a substance to be detected, etc. tend to be adsorbed by the inorganic gel to inhibit the reagent and the reaction product from further developing, so that their distribution concentration in the reagent layer is readily maintained constant. Therefore, more precise measurement of a substance to be detected can be performed.

The substance to be detected in the present invention is not particularly limited as far as it is a substance which is present in the above-mentioned liquid and can be detected by the above-mentioned reagent; for example, as the substance to be detected where the above-mentioned specimen is a biosample: glucose, cholesterol, lactic acid, alkaline phosphatase, etc. may be exemplified. Note that the liquid may be either water-soluble or water-insoluble; generally, it is water-soluble in many cases and it is preferred in the present invention that it is water-soluble.

The method of detecting the above-mentioned substance to be detected is not particularly limited as far as it can detect a reaction between the above-mentioned reagent and substance to be detected; for example, a method of detecting a substance to be detected by an optical change generated by a reaction between the above-mentioned reagent and substance to be detected, a method of detecting a substance to be detected by an electrochemical change generated by a reaction between the above-mentioned reagent and substance to be detected, and the like may be exemplified. In these methods of detecting a substance to be detected, use of reagents that quantitatively react with the substance to be detected as the above-mentioned reagent enables not only detection of the substance to be detected but also enables quantifying of the substance to be detected by measuring an optical change, an electrochemical change, etc.

In the method of detecting a substance to be detected by an optical change, the substance to be detected can be detected by using a substrate made of a light transmitting substance and measuring the above-mentioned optical change by, for example, measurement of transmitted light, measurement of reflected light, etc. Note that as the optical change, generally a coloring reaction by a reaction between the substance to be detected and the above-mentioned reagent may be exemplified but not only coloring but also discoloring, fluorescence, luminescence, etc. may also be exemplified. Also, in the case where the substance to be detected is quantified, for example, measurement of the above-mentioned optical change, where a generally used absorptiometer or fluorometer is utilized or Laman spectrophotometry etc., can be applied.

The method of detecting a substance to be detected by the above-mentioned electrochemical change includes a method in which oxidation-reduction reaction is utilized, a method in which when the substance to be detected is ion, a complex compound that is generated from the ion is utilized, etc.

The method that utilizes the above-mentioned oxidation-reduction reaction includes, for example, a method of using a usually used electrode such as a carbon electrode, reducing or oxidizing an oxidized form or a reduced form of the above-mentioned reagent generated by the oxidation-reduction reaction with a substance to be detected at a potential of the above-mentioned electrode in a range where measurement is possible (in a carbon electrode, usually −1.2V to +1.0 V), and measuring the potential on this occasion to quantify the substance to be detected. Note that the above-mentioned oxidation-reduction reaction may be a reaction in which the substance to be detected and the reagent directly donate and receive electrons or a reaction in which they donate and receive electrons indirectly.

The method of utilizing the above-mentioned complex compound includes, for example, a method of using a liquid membrane electrode provided with a porous polymer layer on the surface of the electrode, impregnating the liquid membrane electrode with the above-mentioned reagent to selectively combine the reagent with the substance to be detected through coordination bond or ionic bond, allowing the resultant to migrate in the polymer layer, and measuring membrane potential generated then to quantify the substance to be detected.

BRIEF DESCRIPTION OF THE DRAWINGS

FIG. 1 is a diagram showing a test strip fabricated according to Example 1 of the present invention;

FIG. 2 is a diagram showing the state of the test strip shown in FIG. 1 in which 1 µl of whole blood is spotted in the reagent layer;

DETAILED DESCRIPTION OF THE PREFERRED EMBODIMENTS

Figure 3:
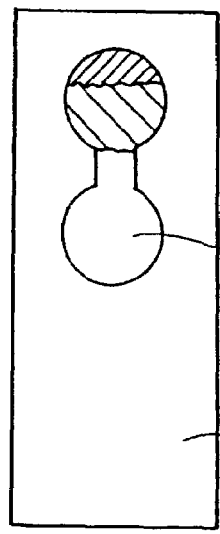
FIG. 3 is a diagram showing the state of the test strip shown in FIG. 1 in which 0.5 µl of whole blood is spotted in the reagent layer.

Hereinafter, examples of the present invention will be presented to more specifically explain the present invention. Note that in the present Examples, test strips using blood (whole blood) as a specimen and glucose (Glc) in blood as a substance to be detected are explained as one example of the present invention.

EXAMPLE 1

First, explanation will be made on a substrate. Note that in the Examples of the present invention, Milli-Q water was used, which was obtained by treating distilled water in Milli-Q Labo (produced by Nippon Millipore Co., Ltd.). The distilled water was produced by using a purified water producing apparatus Autostill WG 220 Model (produced by Yamato Scientific Co., Ltd.).

First, after washing a transparent polystyrene plate with ethanol-Milli-Q water and drying it, it was irradiated with ultraviolet ray in an ultraviolet ray irradiating apparatus (PL16-110, light source: low pressure mercury lamp 110 W, both being produced by Sen Lights Co.) for 1 to 30 minutes (preferably 3 minutes) and subjected to hydrophilicizing treatment of the surface of the above-described transparent polystyrene plate to make a substrate 1. The shape of a hydrophilic area of the substrate 1 was made into a gourd shape formed by coupling two circles having a diameter of 5 mm.

Next, fabrication of a reagent layer will be explained.

Laponite XLG which is the inorganic gelling agent, Bis-Tris buffer solution (pH 6.5), POD (peroxydase), GOD (glucose oxidase), 4-AA (4-aminoantipyrine(4-amino-1,2-dihydro-1,5-dimethyl-2-phenyl-3H-pyrazol-3-one)), and TOOS (N-ethyl-N-(2-hydroxy-3-sulfopropyl)-3-methylaniline), and OTG-2 (average particle size: 4.5 µm) which is a latex bead, were mixed in Mili-Q water to have final concentrations as those shown in Table 1 below, to obtain a colloidal solution (sol) of Laponite XLG.

Note that "U" in Table 1 below is a unit (U: unit) showing the amount of enzyme activity that converts 1 µmol of a substrate into a product per minute at 30° C.

TABLE 1

(Reagent Prescription A)

| Reagent | Manufacturer | Final Concentration |
|---|---|---|
| Raponite XLG | Nippon Silica Industrial Co., Ltd. | 0.5 (% by weight) |
| Bis-Tris | Dojindo Laboratories Co., Ltd. | 0.5 mmol/L |
| POD | Toyobo Co., Ltd. | $7.5 \times 10^3$ U/L |

TABLE 1-continued (Reagent Prescription A)

| Reagent | Manufacturer | Final Concentration |
|---|---|---|
| GOD | Toyobo Co., Ltd. | $25 \times 10^3$ U/L |
| 4-AA | Dojindo Laboratories Co., Ltd. | 7.5 µmol/L |
| TOOS | Dojindo Laboratories Co., Ltd. | 7.5 µmol/L |
| OTG-2 (4.5 µm) | Nippon Paint Co., Ltd. | 12.5 (% by weight) |

The inorganic sol obtained by the above-mentioned operation was spotted at the hydrophilic area of the substrate 1 obtained by the above-mentioned operation and dried at 4° C. for 1 hour to fabricate a reagent layer 2 as shown in FIG. 1.

Next, detection of glucose in blood by the test strip obtained by the above-mentioned operation will be explained.

Figure 4:
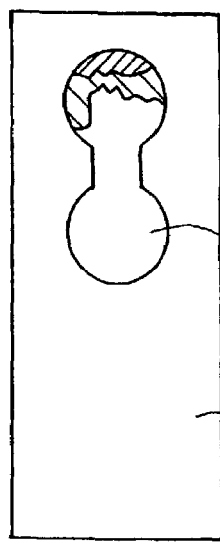
FIG. 4 is a diagram showing the state of the test strip shown in FIG. 1 in which 0.1 µl of whole blood is spotted in the reagent layer.

On the top end of the gourd shape on the reagent layer 2 of each test strip was spotted 1, 0.5 or 0.1 µl of fresh whole blood (fingertip blood). FIGS. 2 to 4 show the states of the test strips when the whole blood was spotted thereto.

First, focusing on the amount of plasma obtained, in the cases of spotting 1 µl and 0.5 µl, plasma in an amount to sufficiently wet the reagent layer 2 of 5 mm in diameter was obtained within 5 seconds as shown in FIGS. 2 and 3. Also, in the case of spotting 0.1 µl, plasma in an amount to wet about ⅔ of the reagent layer 2 of 5 mm in diameter was obtained as shown in FIG. 4. Note that in the case of spotting 1 µl, it was observed that much blood cells and plasma still remained at the site where the whole blood was spotted.

Then, focusing on the response to glucose, the portion wet with plasma was colored pale red and could be sufficiently confirmed by visual observation. This is due mainly to coloring of TOOS ($\lambda_{max}$: 555 nm).

From the above, it can be seen that the test strip of the present invention can detect glucose in plasma by spotting an extremely small amount of whole blood. Also, the test strip of the present invention can be simply fabricated as described above.

EXAMPLE 2

Next, test strips having different thicknesses of reagent layers were fabricated in the same manner as in Example 1 above except that the use amounts of raponite XLG and other reagents was fixed and varied use amount of bead according to Table 2 below, and expected thickness of the reagent layer was measured. Note that expected thickness is a film thickness (µm) obtained by observation of a section of the reagent layer on an SEM and calculation.

On each of the test strips having different thicknesses of reagent layers, whole blood were spotted, and the migration distance of plasma was measured. Note that the migration distance is a distance (mm) of migration of the separated plasma from the location of spotting to the top in 5 seconds counted from the spotting of whole blood.

TABLE 2

| Reagent Prescription | A | A | A | A |
|---|---|---|---|---|
| Amount of bead | ×1.5 | ×1 | ×½ | ×⅓ |
| Final Concentration (% by weight) | 18.75 | 12.50 | 6.25 | 4.16 |
| Expected thickness (µm) | 81 | 54 | 27 | 18 |
| Migration distance (mm) | 8 | 5 | 4 | 2.5 |

As can be seen from Table 2, the thickness of the reagent layer varies depending on the use amount of bead and in the reagent layer having a greater thickness, the migration distance of plasma becomes larger.

EXAMPLE 3

Next, test strips were fabricated in the same manner as in Example 1 above except that each reagent was used in a final concentration as described in Table 3 below. In the same manner as in Example 2 above, the expected thickness of the reagent layer in each test strip was measured and whole blood was spotted to the reagent layer, followed by measurement of the migration distance of plasma on this occasion. Table 3 shows the reagent prescription in each test strip and Table 4 shows measured results of expected thickness and migration distance.

TABLE 3

(Reagent Prescription B, C)

| | Final Concentration | |
|---|---|---|
| Reagent | Prescription B | Prescription C |
| Raponite XLG | 1% | 1.5% |
| Bis-Tris | 1 mmol/L (pH 6.5) | 1.5 mmol/L (pH 6.5) |
| POD | $15 \times 10^3$ U/L | $22.5 \times 10^3$ U/L |
| GOD | $50 \times 10^3$ U/L | $75 \times 10^3$ U/L |
| 4-AA | 15 µmol/L | 22.5 µmol/L |
| TOOS | 15 µmol/L | 22.5 µmol/L |
| OTG-2 | 8.32% | 12.5% |

TABLE 4

| Reagent Prescription | A | A | B | C |
|---|---|---|---|---|
| Amount of bead | ×1 | ×⅓ | ×⅔ | ×1 |
| Final Concentration (% by weight) | 12.50 | 4.16 | 8.32 | 12.50 |
| Expected thickness (µm) | 54 | 18 | 36 | 54 |
| Migration distance (mm) | 5 | 1.5 | 2.5 | 5 |

As can be seen from Tables 3 and 4, if pH is constant, the migration distance of plasma depends on the use amount of bead, i.e., on the thickness of the reagent layer even if the use amount of the reagent is varied more or less.

EXAMPLE 4

Next, test strips were fabricated in the same manner as in Example 1 above except that each reagent was used in a final concentration as described in Table 5 below. Note that in the present example, beads with different particle diameters (4.5 µm and 6.6 µm) were used. In the same manner as in Example 2 above, whole blood was spotted to the reagent layer in each test strip, followed by measurement of the migration distance of plasma on this occasion. Table 5 shows the reagent prescription in each test strip and Table 6 shows measured results of expected thickness and migration distance.

TABLE 5

(Reagent Prescription D, E)

| Reagent | Final Concentration | |
|---|---|---|
| | Prescription D | Prescription E |
| Raponite XLG | 0.5% | 0.5% |
| Phosphate buffer | 0.5 mmol/L (pH 6.0) | 0.5 mmol/L (pH 7.0) |
| POD | $7.5 \times 10^3$ U/L | $7.5 \times 10^3$ U/L |
| GOD | $25 \times 10^3$ U/L | $25 \times 10^3$ U/L |
| 4-AA | 7.5 µmol/L | 7.5 µmol/L |
| TOOS | 7.5 µmol/L | 7.5 µmol/L |
| OTG-2 | 12.5% | 12.5% |

TABLE 6

| Reagent Prescription | A | A | D | E |
|---|---|---|---|---|
| Final Concentration (% by weight) | 12.50 | 12.50 | 12.50 | 12.50 |
| Particle diameter of bead (µm) | 4.5 | 6.6 | 6.6 | 6.6 |
| Migration distance (mm) | 5 | 5 | 3 | 2 |

As can be seen from Tables 5 and 6, if pH is constant the migration distance of plasma does not change even if the particle diameter of bead is varied more or less. The change in migration distance of plasma due to a change in pH is believed to be attributable to a change in the state of blood cells to be separated associated with the change in pH; for example, blood cells migrates in the reagent layer to a more inner portion of the reagent layer due to contraction of blood cells, etc., so that the mobility of plasma in the reagent layer is decreased.

COMPARATIVE EXAMPLE

Reagent layers and test strips were fabricated in the same manner as in Example 1 above except that instead of raponite XLG, HPC-M (hydroxyethylpropyl cellulose: produced by Shin-Etsu Chemical Co., Ltd.), which is a kind of an organic gelling agent, was used in an amount of 2% by weight as a final concentration. Fresh whole blood (fingertip blood) was spotted to the reagent layer of the obtained test strip but plasma did not penetrate into the reagent layer and separation of the spotted whole blood failed.

INDUSTRIAL APPLICABILITY

According to the present invention, upon detection of a substance to be detected from a specimen includes the solid and the liquid, the liquid including the substance to be detected, on a substrate, by forming a reagent layer that is formed from beads and an inorganic gel and that traps the solid to separate the solid and the liquid and that comprises a reagent that causes a detectable reaction with the substance to be detected in the liquid, a test strip, that can measure the substance to be detected even by measurement of transmitted light, that has good oxygen permeability, and that can measure the substance to be detected at high precision, is provided.

What is claimed is:

1. A test strip having an ability of separating a solid from a specimen comprising the solid and a liquid to detect a substance to be detected in the liquid, said test strip comprising:

a reagent layer having a porous structure comprising beads, an inorganic gel, and a reagent that causes a detectable reaction with the substance to be detected to produce a reaction product; and a substrate that supports the reagent layer, wherein the beads are adhered to each other with the inorganic gel and the inorganic gel forms interstices between the beads for trapping the solid components, and further wherein the inorganic gel does not swell and acts as an agent for bonding the beads and can retain the interstices between the beads constant after adsorption of the liquid.

2. The test strip according to claim 1, wherein the specimen is blood including blood cells and plasma.

3. The test strip according to claim 1, wherein the substrate has a hydrophilic area on its surface that supports the reagent layer and supports the horizontal development of the sample in the reagent layer, whereby the solid component and the liquid component can be separated by flowing the specimen horizontally in the same reagent layer.

4. The test strip according to claim 1, wherein the beads have a particle diameter of 0.5 to 10 µm, and the final concentration of the beads is 1 to 30% by weight.

5. The test strip according to claim 1, wherein the inorganic gel adsorbs the reaction product and comprises an inorganic gelling agent at a final concentration of 0.1 to 3% by weight.

6. The test strip according to claim 1, wherein the reagent is a reagent that causes an optical change by reacting with the substance to be detected.

7. The test strip according to claim 1, wherein the substrate is made of a light transmitting substance.

* * * * *

UNITED STATES PATENT AND TRADEMARK OFFICE
CERTIFICATE OF CORRECTION

| | | |
|---|---|---|
| PATENT NO. | : 7,201,871 B2 | Page 1 of 1 |
| APPLICATION NO. | : 10/221644 | |
| DATED | : April 10, 2007 | |
| INVENTOR(S) | : Kaoru Hirai et al. | |

It is certified that error appears in the above-identified patent and that said Letters Patent is hereby corrected as shown below:

On the cover page item (56) References Cited, Foreign Patent Documents, "JP 9-069888" should be -- JP 9-089888 --.

Signed and Sealed this

Twenty-first Day of August, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,201,871 B2 |
| APPLICATION NO. | : 10/221644 |
| DATED | : April 10, 2007 |
| INVENTOR(S) | : Kaoru Hirai et al. |

It is certified that error appears in the above-identified patent and that said Letters Patent is hereby corrected as shown below:

On the cover page of the patent in item (56) References Cited, Foreign Patent Documents, "JP 9-069888" should be -- JP 9-089888 --.

Signed and Sealed this

Twenty-eighth Day of August, 2007

JON W. DUDAS
*Director of the United States Patent and Trademark Office*